(12) United States Patent
Brouwer et al.

(10) Patent No.: US 12,214,304 B2
(45) Date of Patent: Feb. 4, 2025

(54) SEPARATING HYDROCARBONS WITH DIHYDROLEVOGLUCOSENONE OR A DERIVATIVE OF DIHYDROLEVOGLUCOSENONE AS A SOLVENT

(71) Applicant: SHELL USA, INC., Houston, TX (US)

(72) Inventors: Thomas Brouwer, Enschede (NL); Boelo Schuur, Enschede (NL)

(73) Assignee: SHELL USA, INC., Houston, TX (US)

( * ) Notice: Subject to any disclaimer, the term of this patent is extended or adjusted under 35 U.S.C. 154(b) by 127 days.

(21) Appl. No.: 17/913,494

(22) PCT Filed: Apr. 19, 2021

(86) PCT No.: PCT/EP2021/060059
§ 371 (c)(1),
(2) Date: Sep. 22, 2022

(87) PCT Pub. No.: WO2021/213968
PCT Pub. Date: Oct. 28, 2021

(65) Prior Publication Data
US 2023/0201741 A1    Jun. 29, 2023

(30) Foreign Application Priority Data

Apr. 24, 2020   (EP) .................................. 20171367

(51) Int. Cl.
| B01D 3/40 | (2006.01) |
| C07C 7/08 | (2006.01) |
| C10G 21/16 | (2006.01) |

(52) U.S. Cl.
CPC .................. *B01D 3/40* (2013.01); *C07C 7/08* (2013.01); *C10G 21/16* (2013.01)

(58) Field of Classification Search
CPC .... B01D 3/40; C07C 7/08; C07C 7/10; C10G 21/16
See application file for complete search history.

(56) References Cited

U.S. PATENT DOCUMENTS

| 4,134,795 A | 1/1979 | Howat, III |
| 9,505,985 B2 | 11/2016 | Court et al. |
| 2009/0038991 A1* | 2/2009 | Wu .......................... B01D 3/40 422/600 |

FOREIGN PATENT DOCUMENTS

GB    1008921 A    11/1965

OTHER PUBLICATIONS

Speight, The Refinery of the Future, 2011, pp. 117-145 (Year: 2011).*
International Search Report and Written Opinion received for PCT Patent Application No. PCT/EP2021/060059, mailed on Jul. 9, 2021, 8 pages.
Sherwood et al., "Dihydrolevoglucosenone (Cyrene) as a Bio-based Alternative for Dipolar Aprotic Solvents", Chemical Communications, Jul. 1, 2014, vol. 50, Issue No. 68, pp. 9650-9652, XP055246225.
Schuur et al., "Green Solvents for Sustainable Separation Processes", Current Opinion in Green and Sustainable Chemistry, Aug. 1, 2019, vol. 18, pp. 57-65.
Bruyn et al., "Geminal Diol of Dihydrolevoglucosenone as a Switchable Hydrotrope: a Continuum of Green Nanostructured Solvents, "Acs Sustainable Chemistry & Engineering, Mar. 15, 2019, vol. 7, Issue No. 8, pp. 7878-7883.
Pacheco et al., "Intelligent Approach to Solvent Substitution: the Identification of a New Class of Levoglucosenone Derivatives", Chemsuschem, Dec. 20, 2016, vol. 9, Issue No. 24, pp. 3503-3512.
Sprakel et al., "Predicting Solvent Effects on Relative Volatility Behavior in Extractive Distillation Using Isothermal Titration Calorimetry (Itc) and Molecular Modeling (Mm)", Chemical Engineering Science, Dec. 31, 2019, vol. 210.
"Hansen Solubility Parameter", Wikipedia, Aug. 3, 2021, 4 Pages.
Baird et al., "Vapor Pressures, Densities, and Pc-saft Parameters for 11 Bio-compounds", International Journal of Thermophysics, Nov. 6, 2019, vol. 40, Issue No. 102, 36 Pages.
"Sulfolane", Wikipedia, Oct. 27, 2022, 5 Pages.
Mccoy, "New Solvent Seeks to Replace Nmp", Chemical & Engineering News, Jun. 3, 2019, vol. 97, Issue No. 22, p. 14.
Schuur, "Advanced Molecular Separations—Fluid Separations lecture 4", University of Twente, Dec. 6, 2019, 34 Pages.

* cited by examiner

*Primary Examiner* — Renee Robinson
(74) *Attorney, Agent, or Firm* — SHELL USA, INC.

(57) ABSTRACT

The present invention provides a process for separating unsaturated hydrocarbons from a mixture of saturated and unsaturated hydrocarbons, which process comprises the steps of (a) contacting the mixture with a solvent; (b) allowing to form two phases in equilibrium, a first phase comprising solvent and unsaturated hydrocarbons and a second phase comprising the remainder of the mixture; (c) removing the phases separately; and (d) removing from at least one of the phases the hydrocarbons to obtain at least one product stream and regenerated solvent for use in step (a), wherein the solvent comprises dihydrolevoglucosenone or a derivative of dihydrolevoglucosenone.

3 Claims, No Drawings

SEPARATING HYDROCARBONS WITH DIHYDROLEVOGLUCOSENONE OR A DERIVATIVE OF DIHYDROLEVOGLUCOSENONE AS A SOLVENT

CROSS REFERENCE TO RELATED APPLICATIONS

This is a National stage application of International application No PCT/EP2021/060059, filed 19 Apr. 2021, which claims priority of EP application No. 20171367.4, filed 24 Apr. 2020 which is incorporated herein by reference in its entirety.

FIELD OF THE INVENTION

The present invention relates to a process for separating unsaturated hydrocarbons from a mixture of saturated and unsaturated hydrocarbons.

BACKGROUND OF THE INVENTION

A process for separating unsaturated hydrocarbons from a mixture of saturated and unsaturated hydrocarbons comprises the steps of
  (a) contacting the mixture with a solvent;
  (b) allowing to form two phases in equilibrium, a first phase comprising solvent and unsaturated hydrocarbons and a second phase comprising the remainder of the mixture;
  (c) removing the phases separately; and
  (d) removing from at least one of the phases the hydrocarbons to obtain at least one product stream and regenerated solvent for use in step (a).

There are two embodiments of such a process: extractive distillation and liquid-liquid extraction.

Extractive distillation is a process comprising the steps of
  (1) feeding the mixture into a distillation column having a stripping section and a rectifying section located below the stripping section, wherein the mixture is introduced between the stripping section and the rectifying section;
  (2) introducing a solvent at or near the top of the distillation column;
  (3) removing from the bottom of the distillation column a liquid bottom stream comprising solvent and unsaturated hydrocarbons;
  (4) reheating part of the bottom stream to obtain a vapour stream that is introduced into the bottom of the distillation column, below the stripping section;
  (5) removing unsaturated hydrocarbons from the remainder of the bottom stream to obtain a first product stream comprising unsaturated hydrocarbons and regenerated solvent for use in step (2);
  (6) removing from the top of the distillation column a vapour stream comprising the remainder of the mixture;
  (7) condensing the vapour stream and returning at least part of the condensed vapour stream as reflux into the top of the distillation column, and withdrawing the remainder as distillate.

Liquid-liquid extraction is a process comprising the steps of
  (1) feeding the mixture in liquid form together with a solvent into a suitable contactor;
  (2) allowing in the contactor the formation of two phases, a liquid extract comprising solvent and unsaturated hydrocarbons and a liquid raffinate comprising the remainder of the mixture;
  (3) removing the liquid extract from the contactor;
  (4) removing unsaturated hydrocarbons from the liquid extract to obtain a first product stream comprising unsaturated hydrocarbons and regenerated solvent for use in step (1);
  (5) removing the liquid raffinate from the contactor; and
  (6) removing hydrocarbons from the liquid raffinate to obtain a second product stream comprising the remainder of the mixture and regenerated solvent for use in step (1).

A known solvent used in processes where unsaturated hydrocarbons are separated from a mixture of saturated and unsaturated hydrocarbons is sulfolane, tetrahydrothiophene 1,1-dioxide. Sulfolane is used in extractive distillation and as well in liquid-liquid extraction because sulfolane has a higher affinity for unsaturated hydrocarbons than for saturated hydrocarbons.

A disadvantage of sulfolane is that it is not biobased.

It is an object of the present invention to replace sulfolane by a biobased solvent.

SUMMARY OF THE INVENTION

To this end the process for separating unsaturated hydrocarbons from a mixture of saturated and unsaturated hydrocarbons according to the present invention comprises the steps of
  (a) contacting the mixture with a solvent;
  (b) allowing to form two phases in equilibrium, a first phase comprising solvent and unsaturated hydrocarbons and a second phase comprising the remainder of the mixture;
  (c) removing the phases separately; and
  (d) removing from at least one of the phases the hydrocarbons to obtain at least one product stream and regenerated solvent for use in step (a),
  wherein the solvent comprises dihydrolevoglucosenone or a derivative of dihydrolevoglucosenone.

Suitably the process according to the invention comprises the steps of
  (1) feeding the mixture into a distillation column having a stripping section and a rectifying section located below the stripping section, wherein the mixture is introduced between the stripping section and the rectifying section;
  (2) introducing the solvent at or near the top of the distillation column;
  (3) removing from the bottom of the distillation column a bottom stream comprising solvent and unsaturated hydrocarbons;
  (4) reheating part of the bottom stream to obtain a vapour stream that is introduced into the bottom of the distillation column, below the stripping section;
  (5) removing unsaturated hydrocarbons from the remainder of the bottom stream to obtain a first product stream comprising unsaturated hydrocarbons and regenerated solvent for use in step (2);
  (6) removing from the top of the distillation column a vapour stream comprising the remainder of the mixture; and (7) condensing the vapour stream and returning at least part of the condensed vapour stream as reflux into the top of the distillation column, and withdrawing the remainder as distillate.

Alternatively, the invention comprises the steps of (1) feeding the mixture in liquid form together with the solvent into a suitable contactor;
(2) allowing in the contactor the formation of two phases, a liquid extract comprising solvent and unsaturated hydrocarbons and a liquid raffinate comprising the remainder of the mixture;
(3) removing the liquid extract from the contactor;
(4) removing unsaturated hydrocarbons from the liquid extract to obtain a first product stream comprising unsaturated hydrocarbons and regenerated solvent for use in step (1);
(5) removing the liquid raffinate from the contactor; and
(6) removing hydrocarbons from the liquid raffinate to obtain a second product stream comprising the remainder of the mixture and regenerated solvent for use in step (1).

Reference is made to the article 'Dihydrolevoglucosenone (Cyrene) as bio-based alternative for dipolar aprotic solvents', by James Sherwood et al, Chem. Commun., 2014, 50, 9650. In the below Table 1 the Hansen parameters for Cyrene (trade name) are compared with the Hansen parameters for sulfolane. The three Hansen parameters are used to predict if one material will dissolve in a solvent to form a solution, wherein $\delta\_D$ is the parameter for dispersion forces between molecules, $\delta\_P$ is the parameter for dipolar intermolecular forces between molecules and $\delta\_H$ is the parameter for hydrogen bonds between molecules. The unit of the parameters is $MPa^{1/2}$.

TABLE 1

Hansen parameters for Cyrene (trade name) and sulfolane.

|  | Cyrene | Sulfolane |
| --- | --- | --- |
| $\delta\_D$ ($MPa^{1/2}$) | 18.8 | 20.3 |
| $\delta\_P$ ($MPa^{1/2}$) | 10.6 | 18.2 |
| $\delta\_H$ ($MPa^{1/2}$) | 6.9 | 10.9 |

Although in the article is stated that Cyrene (trade name) can replace sulfolane, the Hansen parameters of Cyrene differ substantially from the Hansen parameters of sulfolane. For the sake of completeness we would observe that the article concerns carrying out a reaction in a solvent.

In spite of these differences, it was found that dihydrolevoglucosenone or a derivative of dihydrolevoglucosenone is a suitable solvent in a process for separating unsaturated hydrocarbons from a mixture of saturated and unsaturated hydrocarbons, as will be shown below.

For the sake of clarity, below we will use the name Cyrene without the indication trade name to refer to dihydrolevoglucosenone.

DETAILED DESCRIPTION OF THE INVENTION

The invention will now be described in more details with reference to the below examples.

At first experiments are discussed relating to extractive distillation, wherein first equilibrium data are given, and then, based on these data, a calculated example of extractive distillation is given.

In order to obtain the equilibrium data, a series of experiments had been carried out, with different amounts of methylcyclohexane (MCH), toluene (TOL) and solvent, one for each entry in the below Tables 2a and 2b, wherein the mass ratio of feed (MCH+TOL) to solvent is about 1.

By way of example one experiment of the series is described. In an ebulliometer 9.10 g methylcyclohexane (MCH), 36.1 g toluene (TOL) and 46.2 g Cyrene were mixed at a constant pressure of 1 000 mbar (absolute). The mixture was allowed to equilibrate for about one hour at a temperature of 388.6 K. Then samples of the liquid phase and the condensed vapour phase were drawn and analysed. The liquid phase contained 10.4% m (percent by mass) MCH, 40.8% m TOL and 48.8% m Cyrene. The vapour phase contained 36.3% m MCH, 63.2% m TOL and 0.47% m Cyrene.

For the liquid phase the concentrations of MCH and TOL in the mixture of MCH and TOL are calculated, these concentrations are referred to as relative concentrations. To this end the mass percentage of MCH by the mass percentage of TOL and MCH, $x\_MCH=10.4/(40.8+10.4)=0.203$. Similarly the relative concentration of toluene is $x\_TOL=40.8/(40.8+10.4)=0.797$. The relative concentration of MCH in the vapour phase is $y\_MCH=0.363/(0.363+0.632)=0.365$ and the relative concentration of TOL in the vapour phase is $y\_TOL=0.632/(0.363+0.632)=0.635$. See third row in Table 2a.

The separation factor of is the quotient of two ratios, the nominator of the separation factor is the ratio of the relative concentrations of TOL and MCH in the liquid phase, and the denominator is the ratio of the relative concentrations of TOL and MCH in the vapour phase. The nominator is $x\_TOL/x\_MCH=0.797/0.203=3.926$ and the denominator is $y\_TOL/y\_MCH=0.635/0.365=1.740$. Thus the separation factor is $SF=3.926/1.740=2.257$. Which shows that toluene concentrates preferentially in the liquid phase.

TABLE 2a

Equilibrium data for a quasi binary system, wherein the solvent is Cyrene (according to the invention).

Pressure: 1 000 mbar

Solvent: Cyrene (S:F = 1 mass basis)

| mass fraction MCH | | mass fraction TOL | | temp. | |
| --- | --- | --- | --- | --- | --- |
| (liquid) | (gas) | (liquid) | (gas) | (K.) | SF |
| 0.000 | 0.000 | 1.000 | 1.000 | 383.2 | — |
| 0.119 | 0.223 | 0.881 | 0.777 | 380.7 | 2.125 |
| 0.204 | 0.365 | 0.796 | 0.635 | 389.2 | 2.257 |
| 0.296 | 0.506 | 0.704 | 0.494 | 378.1 | 2.436 |
| 0.396 | 0.616 | 0.604 | 0.384 | 376.8 | 2.447 |
| 0.452 | 0.706 | 0.548 | 0.294 | 375.9 | 2.911 |
| 0.476 | 0.773 | 0.524 | 0.227 | 375.9 | 3.749 |
| 0.618 | 0.841 | 0.382 | 0.159 | 373.9 | 3.269 |
| 0.866 | 0.943 | 0.134 | 0.057 | 374.3 | 2.560 |
| 0.919 | 0.949 | 0.081 | 0.051 | 377.5 | 1.640 |
| 1.000 | 1.000 | 0.000 | 0.000 | 374.0 | — |

TABLE 2b

Equilibrium data for a quasi binary system, wherein
the solvent is sulfolane (not according to the invention).
Pressure: 1 000 mbar
Solvent: sulfolane (S:F = 1 mass basis)

| mass fraction MCH | | mass fraction TOL | | temp. | |
|---|---|---|---|---|---|
| (liquid) | (gas) | (liquid) | (gas) | (K.) | SF |
| 0.000 | 0.000 | 1.000 | 1.000 | 394.3 | — |
| 0.051 | 0.132 | 0.949 | 0.868 | 392.0 | 2.830 |
| 0.093 | 0.240 | 0.907 | 0.760 | 389.2 | 3.080 |
| 0.166 | 0.398 | 0.834 | 0.601 | 384.5 | 3.327 |
| 0.333 | 0.564 | 0.667 | 0.436 | 379.9 | 2.591 |
| 0.404 | 0.645 | 0.596 | 0.355 | 378.3 | 2.680 |
| 0.521 | 0.697 | 0.479 | 0.303 | 376.8 | 2.115 |
| 0.631 | 0.743 | 0.369 | 0.257 | 376.1 | 1.691 |
| 0.728 | 0.799 | 0.272 | 0.201 | 375.9 | 1.485 |
| 0.802 | 0.854 | 0.198 | 0.146 | 375.6 | 1.444 |
| 0.892 | 0.914 | 0.108 | 0.086 | 375.3 | 1.287 |
| 0.918 | 0.937 | 0.082 | 0.063 | 375.2 | 1.329 |

Comparing the results listed in Tables 2a and 2b shows that in particular for low concentrations of TOL in the solvent, the separation factor for the unsaturated hydrocarbon TOL is larger for Cyrene than for sulfolane.

The invention will now be described with reference to an example of extractive distillation, wherein, based on the data presented in Tables 2a and 2b the minimum reflux ratio is calculated for the following conditions.

A mixture of 50 kg MCH and 50 kg TOL is fed at a rate of 100 kg/s, a temperature of 373.15 K and a pressure of 1 bar (absolute) into a distillation column comprising a stripping section arranged below a rectifying section. The mixture is introduced into the distillation column between the stripping section and the rectifying section. A solvent is introduced into the top of the distillation column at a rate of 100 kg/s.

From the bottom of the distillation column a liquid bottom stream comprising solvent and TOL is removed at a rate of 150 kg/s. Part of the liquid bottom stream is reheated and returned as vapour into the bottom of the distillation column, wherein the minimum boil-up ratio is 2.25, where the boil-up ratio is the ratio of the returned vapour mass rate to the mass rate of removal of the remainder of the bottom stream.

From the top of the distillation column a vapour stream comprising the remainder of the mixture is removed at a rate of 50 kg/s. The vapour stream is condensed and part of the condensed vapour stream is returned as reflux into the top of the distillation column, and the remainder is withdrawn a distillate stream.

For these conditions, the minimal reflux ratio is calculated for sulfolane as solvent and for Cyrene as solvent. The reflux ratio is the ratio of the reflux mass rate to the mass rate of removal of the distillate stream. And the minimum reflux ratio is calculated on the assumption that the stripping section has an infinite number of trays.

For sulfolane the calculated minimum reflux ratio is 2.21, whereas for Cyrene the minimum reflux ratio is 1.25. This illustrates the advantage of using Cyrene, because Cyrene allows a smaller minimum reflux ratio, the use of Cyrene enables smaller flows in the distillation column and this reduces the energy costs.

Depending on the temperature of the mixture, it can be can be fed into the distillation column as superheated vapour, saturated vapour, saturated liquid or sub-cooled liquid.

The second example shows the applicability of Cyrene as a solvent in liquid-liquid extraction to remove unsaturated hydrocarbons from a mixture of hydrocarbons. From a series of experiments, of which one is described below, the separation factors were calculated and they are listed in Tables 3a, 3b and 3c.

By way of example one experiment of the series is described. The data for this experiment are included in Table 3a, row 4. In a 10 mL glass vial 2.795 g methylcyclohexane (MCH), 0.227 g toluene (TOL) and 3.018 g Cyrene were mixed and shaken at atmospheric pressure and constant temperature of 298.15 K for at least 12 hours. Afterwards the mixture was left to settle for at least 1 hour. Then the samples of the lighter liquid phase, the raffinate, and heavier liquid phase, the extract, were drawn and analysed. The raffinate contained 92.1% m (percent by mass) MCH, 4.4% m TOL and 3.5% m Cyrene. The extract contained 8.1% m MCH, 3.2% m TOL and 88.7% m Cyrene.

For the raffinate the concentrations of MCH and TOL in the mixture of MCH and TOL are calculated, these concentrations are referred to as relative concentrations. To this end the mass percentage of MCH by the mass percentage of TOL and MCH, x_MCH=92.1/(92.1+4.4)=0.955. Similarly the relative concentration of toluene is x_TOL=4.4/(92.1+4.4)=0.045. The relative concentration of MCH in extract is y_MCH=8.1/(8.1+3.2)=0.72 and the relative concentration of TOL in extract is y_TOL=3.2/(8.1+3.2)=0.28.

The separation factor of is the quotient of two ratios, the nominator of the separation factor is the ratio of the relative concentrations of TOL and MCH in the extract, and the denominator is the ratio of the relative concentrations of TOL and MCH in lighter raffinate. The nominator is y_TOL/y_MCH=0.28/0.72=0.39 and the denominator is x_TOL/x_MCH=0.045/0.955=0.047. Thus the separation factor is SF=0.39/0.047=8.272. Which shows that toluene concentrates preferentially in the extract.

TABLE 3a

Ternary system data and separation factor for
Cyrene at 298.15K and a pressure of 1 bar (absolute).

| Mass fraction the raffinate | | | Mass fraction in the extract | | | |
|---|---|---|---|---|---|---|
| Cyrene | TOL | MCH | Cyrene | TOL | MCH | SF |
| 0.021 | 0.008 | 0.971 | 0.913 | 0.007 | 0.079 | 12.005 |
| 0.028 | 0.015 | 0.957 | 0.914 | 0.012 | 0.074 | 10.418 |
| 0.032 | 0.029 | 0.940 | 0.897 | 0.023 | 0.080 | 9.334 |
| 0.035 | 0.044 | 0.921 | 0.887 | 0.032 | 0.081 | 8.272 |
| 0.037 | 0.059 | 0.904 | 0.876 | 0.042 | 0.082 | 7.947 |
| 0.067 | 0.152 | 0.781 | 0.606 | 0.208 | 0.186 | 5.719 |
| 0.140 | 0.314 | 0.546 | 0.458 | 0.321 | 0.222 | 2.517 |
| 0.050 | 0.093 | 0.857 | 0.871 | 0.056 | 0.073 | 6.971 |
| 0.120 | 0.219 | 0.661 | 0.740 | 0.149 | 0.110 | 4.090 |

TABLE 3b

Ternary system data and separation factor for
Cyrene at 323.15K and a pressure of 1 bar (absolute).

| Mass fraction in the raffinate | | | Mass fraction in the extract | | | |
|---|---|---|---|---|---|---|
| Cyrene | TOL | MCH | Cyrene | TOL | MCH | SF |
| 0.059 | 0.006 | 0.935 | 0.936 | 0.003 | 0.061 | 6.772 |
| 0.065 | 0.015 | 0.920 | 0.907 | 0.008 | 0.085 | 5.830 |
| 0.059 | 0.032 | 0.909 | 0.898 | 0.017 | 0.085 | 5.624 |

TABLE 3b-continued

Ternary system data and separation factor for Cyrene at 323.15K and a pressure of 1 bar (absolute).

| Mass fraction in the raffinate | | | Mass fraction in the extract | | | |
| --- | --- | --- | --- | --- | --- | --- |
| Cyrene | TOL | MCH | Cyrene | TOL | MCH | SF |
| 0.062 | 0.046 | 0.892 | 0.892 | 0.023 | 0.094 | 5.344 |
| 0.068 | 0.061 | 0.871 | 0.905 | 0.025 | 0.070 | 5.225 |
| 0.138 | 0.151 | 0.711 | 0.792 | 0.084 | 0.124 | 3.220 |
| 0.152 | 0.181 | 0.667 | 0.693 | 0.134 | 0.173 | 2.856 |
| 0.204 | 0.218 | 0.578 | 0.624 | 0.171 | 0.205 | 2.203 |
| 0.257 | 0.241 | 0.502 | 0.564 | 0.196 | 0.239 | 1.712 |

TABLE 3c

Ternary system data and separation factor for Cyrene at 348.15K and a pressure of 1 bar (absolute).

| Mass fraction in the raffinate | | | Mass fraction in the extract | | | |
| --- | --- | --- | --- | --- | --- | --- |
| Cyrene | TOL | MCH | Cyrene | TOL | MCH | SF |
| 0.178 | 0.006 | 0.816 | 0.920 | 0.003 | 0.077 | 4.865 |
| 0.191 | 0.014 | 0.794 | 0.916 | 0.007 | 0.077 | 5.315 |
| 0.191 | 0.029 | 0.780 | 0.875 | 0.018 | 0.107 | 4.595 |
| 0.207 | 0.043 | 0.750 | 0.871 | 0.024 | 0.105 | 4.125 |
| 0.196 | 0.056 | 0.749 | 0.853 | 0.034 | 0.113 | 4.001 |
| 0.354 | 0.125 | 0.522 | 0.737 | 0.085 | 0.178 | 2.009 |

The relatively large separation factors show that toluene, the unsaturated hydrocarbon, is concentrated preferentially in the heavier phase, the extract. And thus the unsaturated hydrocarbon is extracted from the mixture into the extract.

Examples of derivatives of dihydrolevoglucosenone are so-called Cygnets, such as (1R, 5S)-7,8-dioxaspiro[bicycle[3.2.1]octane-2,2'-[1,3]dioxane] (Cygnet 0.0); (1R,5S)-4'-methyl-7,8-dioxaspiro[bicycle[3.2.1]octane-2,2'-[1,3]dioxane] (Cygnet 1.0) and (1R,5S)-4', 5'-dimethyl-7,8-dioxaspiro[bicycle[3.2.1]octane-2,2'-[1,3] dioxane](Cygnet 1.1).

Other derivatives of dihydrolevoglucosenone are ((1R, 5S)-7,8-dioxaspiro[bicycle[3.2.1]octane-2,2'-[1,3]dioxane]-4'-yl) methanol; (1S,5R)-6,8-dioxabicyclo[3.2.1]octan-4-ol; (1S,4R, 6R, 11S)-9-methyl-1,6,7,8,11,12-hexahydro-2H-1,4-epoxycyclohepta[d]oxepin-5 (4H)-oneone; (1S,5R)-4-methoxy-6,8-dioxabicyclo[3.2.1]octane; methyl-2-(((1S,5R)-6,8-dioxabicyclo[3.2.1]octan-4-yl)oxy)acetate; and (1S,5R)-6,8-dioxabicyclo[3.2.1]octane-4-carboxylic acid.

We claim:

1. Process for separating unsaturated hydrocarbons from a mixture of saturated and unsaturated hydrocarbons, which process comprises the steps of
   (a) contacting the mixture with a solvent;
   (b) allowing to form two phases in equilibrium, a first phase comprising solvent and unsaturated hydrocarbons and a second phase comprising the remainder of the mixture;
   (c) removing the phases separately; and
   (d) removing (i) unsaturated hydrocarbons from the first phase, (ii) saturated hydrocarbons from the second phase, or (iii) unsaturated hydrocarbons from the first phase and saturated hydrocarbons from the second phase, to obtain at least one product stream and regenerated solvent for use in step (a),
   wherein the solvent comprises dihydrolevoglucosenone.

2. Process according to claim 1, comprising the steps of
   (1) feeding the mixture into a distillation column having a stripping section and a rectifying section, wherein the mixture is introduced between the stripping section and the rectifying section;
   (2) introducing the solvent into the top of the distillation column;
   (3) removing from the bottom of the distillation column a bottom stream comprising solvent and unsaturated hydrocarbons;
   (4) reheating part of the bottom stream to obtain a vapour stream that is introduced into the bottom of the distillation column;
   (5) removing unsaturated hydrocarbons from the remainder of the bottom stream to obtain a first product stream comprising unsaturated hydrocarbons and regenerated solvent for use in step (2);
   (6) removing from the top of the distillation column a vapour stream comprising the remainder of the mixture; and
   (7) condensing the vapour stream and returning a first part of the condensed vapour stream as reflux into the top of the distillation column, and withdrawing the remaining second part of the condensed vapour stream as distillate.

3. Process according to claim 1, comprising the steps of
   (1) feeding the mixture in liquid form together with the solvent into a contactor;
   (2) allowing in the contactor the formation of two phases, a liquid extract comprising solvent and unsaturated hydrocarbons and a liquid raffinate comprising the remainder of the mixture;
   (3) removing the liquid extract from the contactor;
   (4) removing unsaturated hydrocarbons from the liquid extract to obtain a first product stream comprising unsaturated hydrocarbons and regenerated solvent for use in step (1);
   (5) removing the liquid raffinate from the contactor; and
   (6) removing hydrocarbons from the liquid raffinate to obtain a second product stream comprising the remainder of the mixture and regenerated solvent for use in step (1).

* * * * *